US00PP35780P2

(12) United States Plant Patent
Olesen

(10) Patent No.: US PP35,780 P2
(45) Date of Patent: Apr. 30, 2024

(54) MINIATURE ROSE PLANT NAMED 'POULPAH115'

(50) Latin Name: *Rosa hybrida*
Varietal Denomination: Poulpah115

(71) Applicant: Mogens Nyegaard Olesen, Fredensborg (DK)

(72) Inventor: Mogens Nyegaard Olesen, Fredensborg (DK)

(73) Assignee: Poulsen Roser Als, Fredensborg (DK)

( * ) Notice: Subject to any disclaimer, the term of this patent is extended or adjusted under 35 U.S.C. 154(b) by 0 days.

(21) Appl. No.: 18/445,485

(22) Filed: Sep. 8, 2023

(51) Int. Cl.
*A01H 5/02* (2018.01)
*A01H 6/74* (2018.01)

(52) U.S. Cl.
USPC ..... Plt./128

(58) Field of Classification Search
USPC ..... Plt./128, 121, 148
CPC . A01H 5/02; A01H 5/00; A01H 6/749; A01H 6/74
See application file for complete search history.

(56) References Cited

U.S. PATENT DOCUMENTS

PP29,725 P2 * 10/2018 Olesen ..... Plt./121

OTHER PUBLICATIONS

CPVO Register Version 4.12.14, retrieved on Nov. 20, 2023 at https://online.plantvarieties.eu/publicConsultationDetails?registerId=20222163&denomination=poulpah115, 2 pp. (Year: 2023).*

* cited by examiner

*Primary Examiner* — June Hwu

(57) ABSTRACT

A new garden rose plant of the Miniature class which has abundant, mauve pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah115'.

This application claims priority to Plant Breeder's Rights Application Number 2022/2163, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah115', originated as a single seedling from the stated cross.

The new variety may be distinguished from its male pollen parent and female seed parent primarily by the following characteristics. The male pollen parent plant has light red flowers while the new variety has mauve pink flowers. The female seed parent plant has light red flowers while the new variety has mauve pink flowers.

The objective of the hybridization of this rose variety was to create a new and distinct variety with unique qualities, such as:

1. Uniform and abundant mauve pink flowers;
2. Vigorous, but compact growth when propagated on its own roots;
3. Exceptional disease resistance.

This combination of qualities is not present in previously available commercial cultivars of this type, known to the inventor, and distinguish 'Poulpah115' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah115' was selected in the spring of 2016 by the inventor as a single plant from the progeny of the aforementioned hybridization.

Asexual reproduction of 'Poulpah115' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah115' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah115'.

Specifically illustrated in FIG. 1 of the drawings are open flowers viewed from above and the side, a flower bud upon opening, petals detached, and sepals detached revealing reproductive flower parts.

Figure 1:
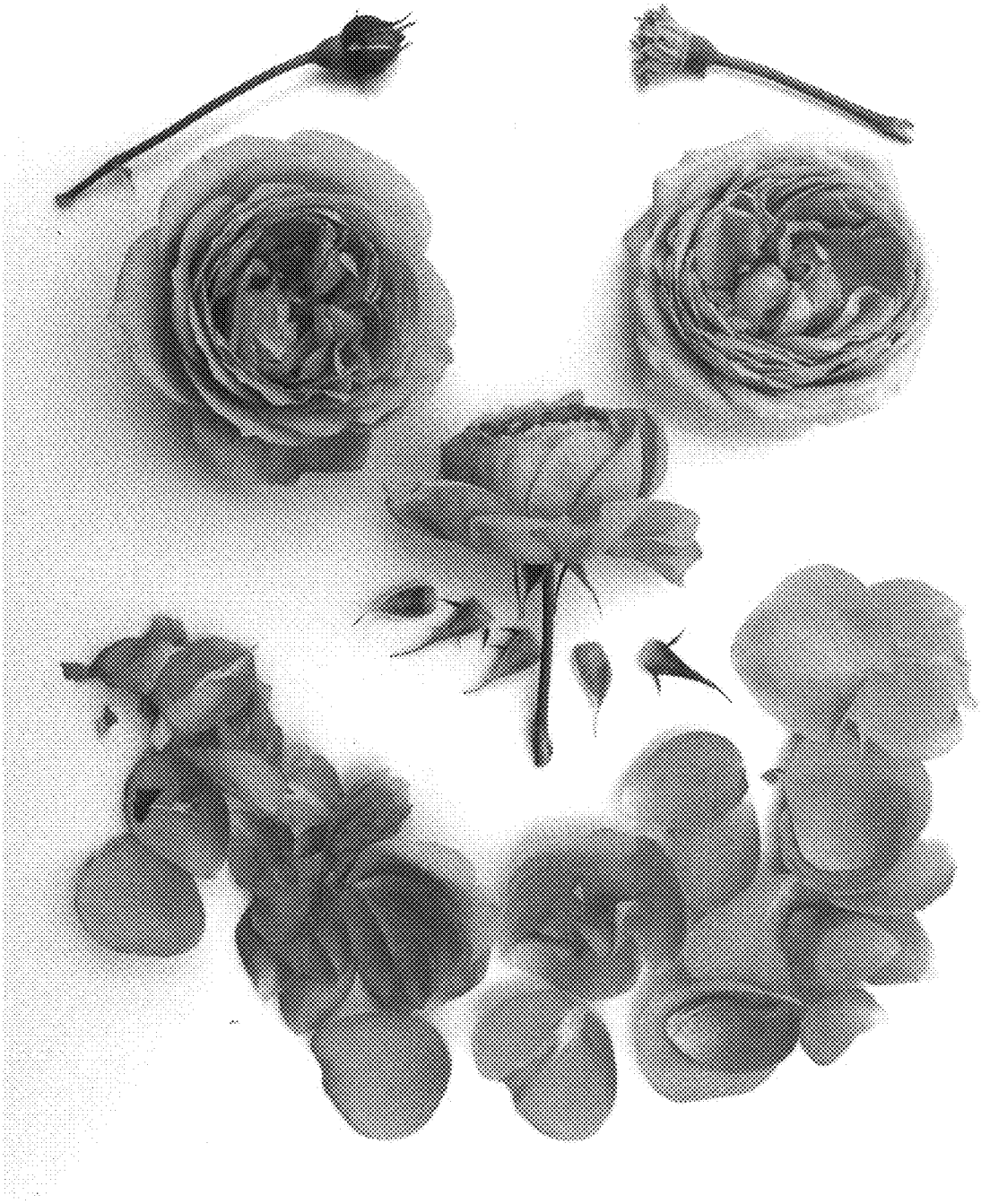
Figure 2:
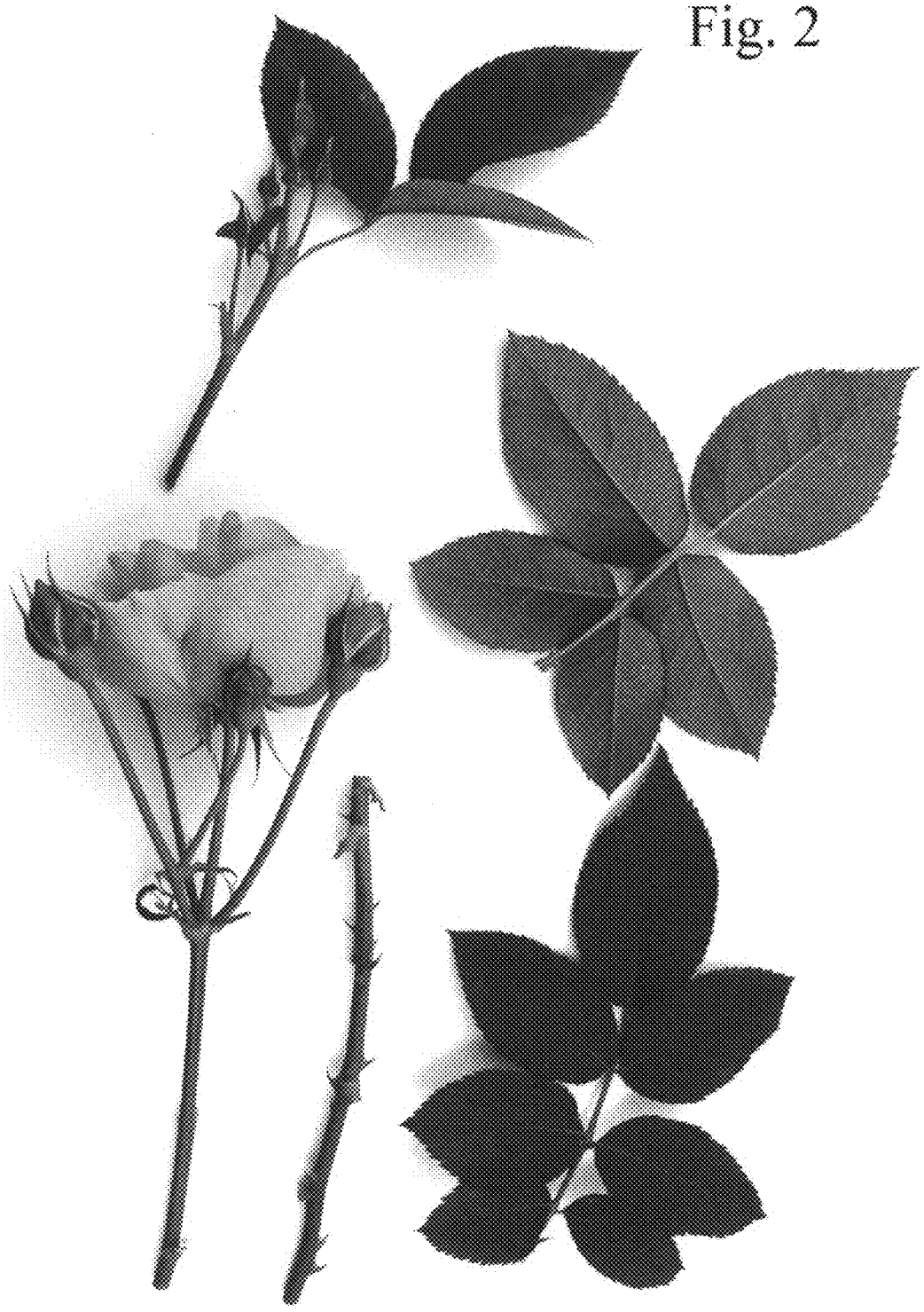

Specifically illustrated in FIG. 2 of the drawings are a cluster of flowers on the branch, mature and juvenile leaves, and a bare stem exhibiting prickles.

Plants shown are 5 months of age.

DETAILED DESCRIPTION OF THE VARIETY

The following is a description of 'Poulpah115', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah092', U.S. Plant Pat. No. 29,725 are compared to the claimed plant. While 'Poulpah115' has 62 flower petals, 'Poulpah092' has 45 flower petals. The claimed plant has a strong citrus perfume, while 'Poulpah092' has a moderate perfume scent. Open flowers of 'Poulpah115' are generally Red-Purple Group 73B, Purple Group 75C after 10 days, while 'Poulpah092' has a general tonality of Red-Purple Group 69A.

Flower and Flower Bud

Blooming habit: Continuous.

Flower bud:

- *Size.*—Upon opening, 23 mm in length from base of receptacle to end of bud. Bud diameter is 13 mm.
- *Bud form.*—Ovoid.
- *Bud color.*—As sepals divide petals are Red-Purple Group 61B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—30 mm long, 8 mm wide.
- *Receptacle.*—Texture: Smooth. Size: 8 mm in height, 7 mm wide. Color: Yellow-Green Group 144A. Shape: Campanulate.
- *Pedicel.*—Surface: Smooth. Length: 50 to 55 mm. Diameter: 2 mm on average. Color: Yellow-Green Group 144A. Strength: Strong.
- *Peduncle.*—Length: 2 to 3 cm. Diameter: About 3 mm. Color: Yellow-Green Group 144A. Texture: Smooth.

Flower bud development: Flower buds are borne in clusters of 3 to 8 flower buds per stem.

Flower bloom:

- *Fragrance.*—Strong, citrus perfume.
- *Duration.*—The blooms have a duration on the plant of approximately 18 days. Petals fall cleanly away from plant after flowers have fully matured.
- *Size.*—Flower diameter is 75 mm when open. Flower depth is 35 mm.
- *Flower shape.*—Open cup, double flower, with petals that curve out from the center.
- *Shape of flower, side view.*—The upper portion is flat. The lower portion is flat concave.

Petalage: Under normal conditions, flowers have about 62 petals.

General tonality of flower: Open flowers are Red-Purple Group 73B. After 10 days Purple Group 75C.

Petal color:

- *Upon opening, outer petals.*—Upper surface: Red-Purple Group 73A. Lower surface: Red-Purple Group 73C.
- *Upon opening, inner petals.*—Upper surface: Red-Purple Group 73A. Lower surface: Red-Purple Group 73B.
- *Basal petal spots, upon opening.*—Upper surface: Small Yellow Group 4C. Lower surface: Small Yellow Group 4C.
- *After opening, outer petals.*—Upper surface: Red-Purple Group 73A, 73B blend. Lower surface: Purple Group 75C with streaks of Red-Purple Group 73A.
- *After opening, inner petals.*—Upper surface: Red-Purple Group 73A. Lower surface: Red-Purple Group 73B.
- *Basal petal spots, after opening.*—Upper surface: Yellow Group 4D. Lower surface: Yellow Group 4D.

Petals:

- *Petal reflex.*—Partially reflexed.
- *Margin.*—Entire and uniform with occasional cleft. Light undulations.
- *Shape.*—Broad and elliptic. Apex shape: Rounded. Base shape: Acute.
- *Size.*—42 mm (l)×50 mm (w).
- *Texture.*—Smooth.
- *Thickness.*—Average.

Petaloids:

- *Size.*—25 mm (l) by 20 mm (w).
- *Quantity.*—About 10.
- *Shape.*—Elliptical with an acute base and rounded apices.
- *Color.*—Red-Purple Group 73A with streaks Yellow Group 4D.

Reproductive flower parts:

- *Pollen.*—None observed.
- *Anthers.*—Size: 3 mm in length. Color: Greyed-Orange Group N163C. Quantity: 40 on average.
- *Filaments.*—Color: Yellow Group 13. Length: 6 mm.
- *Pistils.*—Length: 6 mm. Quantity: 31 on average.
- *Stigmas.*—Color: Greyed-Yellow Group 162D.
- *Styles.*—Color: Greyed-Yellow Group 162D.
- *Location of stigmas.*—Inferior in location relative to the length of the filaments and the height of the anthers.
- *Hips.*—None Observed.

Plant

Plant growth: Upright. Plants are about 42 cm in height, and 35 cm wide.

Stems:

- *Color of juvenile growth.*—Yellow-Green Group 144A.
- *Color of mature growth.*—Yellow-Green Group 144A.
- *Length.*—Canes are about 15 cm from the base of the plant to the flowering portion.
- *Diameter.*—About 4 mm.
- *Internodes.*—On mature canes about 30 mm between nodes.
- *Surface texture.*—Young wood: Smooth. Older wood: Smooth.

Long prickles:

*Incidence.*—On average 7 prickles per 10 cm of stem.

*Size.*—Average length of prickles on mature stems is 6 mm.

*Shape.*—Upper portion is convex. Lower portion is deep concave.

*Color.*—Juvenile prickles: Yellow-Green Group 144A. Mature prickles: Greyed-Orange Group 166D.

Plant foliage:

*Compound leaf.*—155 mm (l)×135 (w).

*Quantity.*—2 or 3 leaves per 10 cm of stem on average.

*Leaf bearing angle to the stem.*—90 degrees.

*Color of juvenile foliage.*—Upper side: Yellow-Green Group 146B with marginal intonations of Greyed-Orange Group 166A. Lower side: Yellow-Green Group 147C.

*Color of mature foliage.*—Upper side: Yellow-Green Group 147A. Lower side: Yellow-Green Group 147B.

Plant leaves and leaflets:

*Stipules.*—Size: 13 mm long, 2 mm wide. Quantity: 2 per compound leaf. Shape: Linear, slightly broad based with outward extending apices. Margins: Finely serrated. Color: Yellow-Green Group 144A.

*Petiole.*—Length: 18 mm. Diameter: 2 mm. Upper surface color: Yellow-Green Group 144A. Lower surface color: Yellow-Green Group 144A.

*Rachis.*—Length: 56 mm. Upper surface color: Yellow-Green Group 144A. Lower surface color: Yellow-Green Group 144A.

*Leaflet.*—Quantity: Normally 5 to 7 leaflets. Margins: Serrated. Size: Terminal leaflets are about 72 mm long, 40 mm wide. Shape: Generally elliptical. Base: Rounded. Apex: Acuminate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah115' substantially as described and illustrated herein.

* * * * *